United States Patent [19]

Taylor et al.

[11] Patent Number: 5,347,475
[45] Date of Patent: Sep. 13, 1994

[54] METHOD FOR TRANSFERRING SPECTRAL INFORMATION AMONG SPECTROMETERS

[75] Inventors: James L. Taylor; Jay C. Knepper, both of Naperville, Ill.

[73] Assignee: Amoco Corporation, Chicago, Ill.

[21] Appl. No.: 764,147

[22] Filed: Sep. 20, 1991

[51] Int. Cl.$^5$ .......................... G01J 3/02; G06F 15/42
[52] U.S. Cl. .............................. 364/571.01; 364/496; 364/570; 364/498; 356/326
[58] Field of Search ............. 364/570, 571.01, 571.04, 364/571.05, 498, 496, 497; 356/325, 328; 250/339

[56] References Cited

U.S. PATENT DOCUMENTS

| | | |
|---|---|---|
| 4,171,913 | 10/1979 | Wildy et al. ........................ 356/325 |
| 4,744,657 | 5/1988 | Aralis et al. .................... 364/498 X |
| 4,847,793 | 7/1989 | Cygnarowicz et al. ............ 364/570 |
| 4,959,796 | 9/1990 | Hidaka et al. ....................... 364/497 |
| 5,116,122 | 5/1992 | Fukuma .............................. 356/326 |
| 5,119,315 | 6/1992 | Kemp et al. ........................ 364/498 |
| 5,206,701 | 4/1993 | Taylor et al. ....................... 356/326 |

Primary Examiner—Kevin J. Teska
Attorney, Agent, or Firm—Thomas A. Yassen; Richard A. Kretchmer

[57] ABSTRACT

A method is provided for transferring spectral information, comprising spectral images, from a source spectrometer to a target spectrometer in order that chemometric models can be transferred among spectrometers. The method comprises passing substantially monochromatic atomic lines into a source and target spectrometer and displaying a spectrum of light intensity for each spectrometer, developing a correlation between the spectra of light intensity such that the location and shape of the target spectrometer correlated spectrum can be expressed as a function of the source spectrometer, processing a known sample into the source spectrometer and displaying spectral images, developing a transformation for the spectral images from the source spectrometer such that the correlated and transformed spectral images are transformed to appear substantially similar to the spectral images of the sample measured with the target spectrometer, and generating a chemometric model to relate the correlated and transformed spectral images from the target spectrometer to the physical properties of the sample corresponding to the spectral images.

28 Claims, 1 Drawing Sheet

METHOD FOR TRANSFERRING SPECTRAL INFORMATION AMONG SPECTROMETERS

BACKGROUND OF THE INVENTION

This invention relates to an improved method for the utilization of spectrometers. More particularly, this invention relates to an improved method for transferring spectral information, including chemometric models, among spectrometers.

The physical properties of sample materials, which, for purposes of the present invention encompass the physical, chemical, and fuel properties of sample materials, have historically been measured one property at a time, utilizing test methods which have been developed to specifically evaluate one particular property. For example, the heat of formation of a particular sample has been determined by actually burning the sample in a calorimeter. Similarly, the molecular weight of a sample has been determined by inducing and measuring viscous flow of the sample using a viscometer. In each of these examples, however, the physical test methods measure, or quantify, the physical properties by actually subjecting the sample to the conditions in question. To measure more than one physical property of a particular sample, a plurality of tests must be individually conducted on a plurality of samples. Often these samples are destroyed or consumed in the process. These approaches to measuring physical properties are slow, expensive, subject to testing inconsistency, and do not facilitate on-line or real time use in an industrial or field setting.

More recently, spectrophotometric analysis has been used to determine indirectly the quantitative properties of sample materials.

U.S. Pat. No. 4,800,279 to Hieftje et al. discloses a method for utilizing near-infrared absorbance spectra to identify the physical properties of gaseous, liquid, or solid samples. The method requires measuring and recording the near-infrared absorbance spectra of a representative field of calibration samples and employing a row-reduction algorithm to determine which wavelengths in the near-infrared spectrum, and associated weighting constants, are statistically correlated to the physical property being quantified. The near-infrared absorbance of a sample can then be measured at each of the correlated wavelengths and corrected by the corresponding weighting constants. The physical property being quantified is then computed from the corrected measure of the absorbance of the sample at the correlated wavelengths.

Use of spectrophotometric analysis has numerous advantages over other methods since it is rapid, relatively inexpensive, and multivariate in that many properties can be tested for simultaneously. There is theoretically great potential for spectrophotometric analysis in manufacturing facilities, chemical plants, petroleum refineries, and the like. However, several obstacles must be overcome in order to achieve successful implementation from a practical viewpoint.

Chemometric predictions are particularly sensitive to aberrations in the sample spectra and in the spectra developed from the original calibration standards. These spectra are generally presented as plots of optical wavelength, frequency of radiation, or the like (x-axis) and absorbance, transmittance, or intensity of light (y-axis). The wavelength measurements can be, and are generally made over a range of at least 100 nanometers. Shifts of 0.01 nanometers in the wavelength axis can produce measurable and often sizeable errors in predictions. When chemometric models are used directly on another seemingly identical spectrometer (i.e. produced by the same manufacturer and having the same model number). the predictions can be and are generally grossly inaccurate. Often, chemometric models have to be rebuilt after simple repairs or maintenance of a spectrometer. The model rebuilding step can require the collection and the analysis of from 20 to 100 samples prior to proceeding with chemometric model rebuilding. These activities are costly, time consuming, and subject the model to additional errors in laboratory analysis.

Several patents teach methods for calibrating single spectrometers or cross-correlating among spectrometers, each method achieving varying degrees of success and imposing limitations as to its use.

U.S. Pat. No. 4,744,657 to Aralis et al. discloses a method for calibrating a single spectrometer, suitable for use with spectrometers having a monochromatic light source. The method addresses calibration of the photometric axis (light intensity) only and avoids the necessity of addressing variances in the wavelength axis by using a light source having a series of monochromatic lines. While single-wavelength monochromatic spectrometers can be easier to calibrate, they are limited as to the wavelengths that can be monitored, resulting in the frequent switching of wavelengths and light sources and resulting in numerous calibrations. Moreover, outside of a controlled laboratory environment, optical components are subjected to external stresses which can cause drift in the baseline. This drift is generally eliminated by filtering techniques which require measurements of light intensity at consecutive wavelengths rather than at a single wavelength.

U.S. Pat. No. 4,779,216 to Collins discloses a two-stage interactive method for calibrating a single spectrometer having a polychromatic light source. The method requires use of a large number of monochromatic spectral lines (approximately 100 lines) and a small spectral window to obtain precise wavelength calibration. An iterative, self-consistent, discrete Fouder transform is used for the determination of multiple positioning correction terms. When the Fourier calculations are completed, the results of the calibration procedure are presented to a skilled analyst for acceptance. The method requires use of complex Fourier transforms, relies extensively on skilled analyst intervention to accomplish the calibration, and is generally limited to use on moving grating spectrometers or other spectrometers where the resolution can be varied.

U.S. Pat. No. 4,866,644 to Shenk et al. discloses a method for cross-correlating spectrometers by the statistical treatment of spectra for several representative samples of the material to be analyzed. The method involves measuring the spectra of the representative samples on both spectrometers and developing statistical correlations to permit the use of spectral information obtained from one instrument on the second instrument. The representative samples are generally maintained and stored in an extensive sample library for future calibrations. The use of extensive sample libraries can be inconvenient and difficult to utilize in an industrial environment, especially in facilities where several spectrometers are actively in use. Furthermore, there is no guarantee that the sample properties will not change during storage due to chemical instability and contamination.

The above U.S. Patents teach methods of calibrating single spectrometers or transferring spectral information among spectrometers requiring the intervention of a skilled analyst or the use of training or representative samples. The above methods are generally not suitable for transferring chemometric models in an industrial environment or setting and all would create adversity to the successful election, selection, and implementation of spectroscopy equipment in such an environment. In order to realize the potential benefits of spectrophotometrics in manufacturing facilities, chemical plants, petroleum refineries, and the like, a method is required whereby the impediments to accurate transfer of chemometric correlations are identified, quantified, and solved.

It is therefore an object of the present invention to provide a method of transferring spectral information among spectrometers that achieves superior transfer accuracy.

It is an object of the present invention to provide a method of transferring spectral information among spectrometers that does not require the use of training or representative samples.

It is another object of the present invention to provide a method of transferring spectral information among spectrometers that is simple and convenient and can be performed by a semi-skilled technician, a computer, and a procedural guideline.

It is another object of the present invention to provide a method of transferring spectral information among spectrometers that can be performed without intervening decision-making steps by a skilled analyst.

It is yet another object of the present invention to provide a process for determining the physical properties of samples utilizing spectrometers utilizing spectral information transferred from another spectrometer.

Other objects appear herein.

SUMMARY OF THE INVENTION

The above objects can be attained utilizing the method of the present invention. The present invention comprises a method for transferring spectral information comprising spectral images, from a source spectrometer to a target spectrometer in order that chemometric models can be transferred from the source spectrometer to the target spectrometer. The method comprises:

(a) transforming the spectral images of a sample measured on the source spectrometer, the sample having known physical properties, onto the target spectrometer in a manner such that the transformed spectral images appear substantially similar to the spectral images of the sample measured on the target spectrometer by correlating the wavelength scales of the source and target spectrometers utilizing substantially monochromatic atomic lines;

(b) generating a chemometric model to relate the transformed spectral images from the target spectrometer to the physical properties of the sample corresponding to the spectral images.

In a process embodiment, a target spectrometer comprising a chemometric model, transferred from a source spectrometer in a manner similar to that described herein, is utilized to determine at least one physical property of at least one sample.

It has been found that a method for transferring spectral information comprising a step for correlating the wavelength scales of a source and target spectrometer comprising monochromatic lines and the particular steps described herein can substantially improve spectral information transfer accuracy between spectrometers. Correction or adjustment steps for other disparities such as background spectra and path length differences further enhance the accuracy and applicability of the method.

The present invention provides a method for transferring spectral information among spectrometers having outstanding accuracy. The method generally provides a transferred chemometric model on the target spectrometer (the spectrometer receiving the chemometric model) having nearly the same accuracy as the chemometric model on the source spectrometer (the spectrometer transferring the chemometric model). The increase in the standard error of prediction for the target spectrometer as compared to the source spectrometer is generally less than 30° percent relative to the standard error of prediction for the source spectrometer and can range as low as 10° percent. For example, where the chemometric model on the source spectrometer has a standard error of prediction of 0.10 percent, the transferred chemometric model on the target machine would be transferred with an error of prediction of less than 0.13 percent. At the ranges of accuracy attendant to spectrometers suitable for use in conjunction with the method of the present invention, the accuracy levels of the target spectrometer and the source spectrometer are essentially equivalent.

The method of the present invention provides a method for transferring spectral information among spectrometers that does not require the use of training or representative samples. An array of calibration samples can be employed during the original calibration of the source spectrometer, but are not utilized or necessary after the initial calibration of the source spectrometer. Subsequent transfers of spectral information from the source spectrometer to one or more target spectrometers is performed directly from the source spectrometer to the target spectrometer through the method described. Eliminating the need for training or representative samples eliminates the need to handle, store, and administrate sample storage and eliminates the risk of the samples changing during storage. Training sample methods are also difficult and unwieldy to administer in an industrial environment, especially where the spectrometer is in a location that provides little maneuvering room or where the spectrometer is positioned in a location requiring special agility, such as the climbing of ladders.

The method of the present invention provides a method for transferring spectral information among spectrometers that is simple and convenient and can be performed by a semi-skilled technician, a computer, and a procedural guideline. The method of the present invention has been developed in a manner that requires the temporary removal of the polychromatic light source, replacement with a suitable monochromatic light source, and the execution of precise method steps that can be provided substantially through computer software. Moreover, the source spectrometer spectral information can be recorded at any time prior to transfer of spectral information and can be provided through a data storage device separate and apart from the spectrometer, which further minimizes task complexity, the time required for transfer, and the potential for error. These factors are particularly critical in an industrial environment.

The method of the present invention provides a method of transferring spectral information among spectrometers that can be performed without intervening decision-making steps by a skilled analyst. The method of the present invention requires minimal operator judgement, technical assessment, and decision-making skills beyond that of temporarily changing a light source and implementing software routines. This method can be executed in its entirety by instrumentation personnel such as those that routinely maintain, install, and calibrate conventional instrumentation in manufacturing facilities, chemical plants, petroleum refineries, and the like.

BRIEF DESCRIPTION OF THE INVENTION

Figure 1:
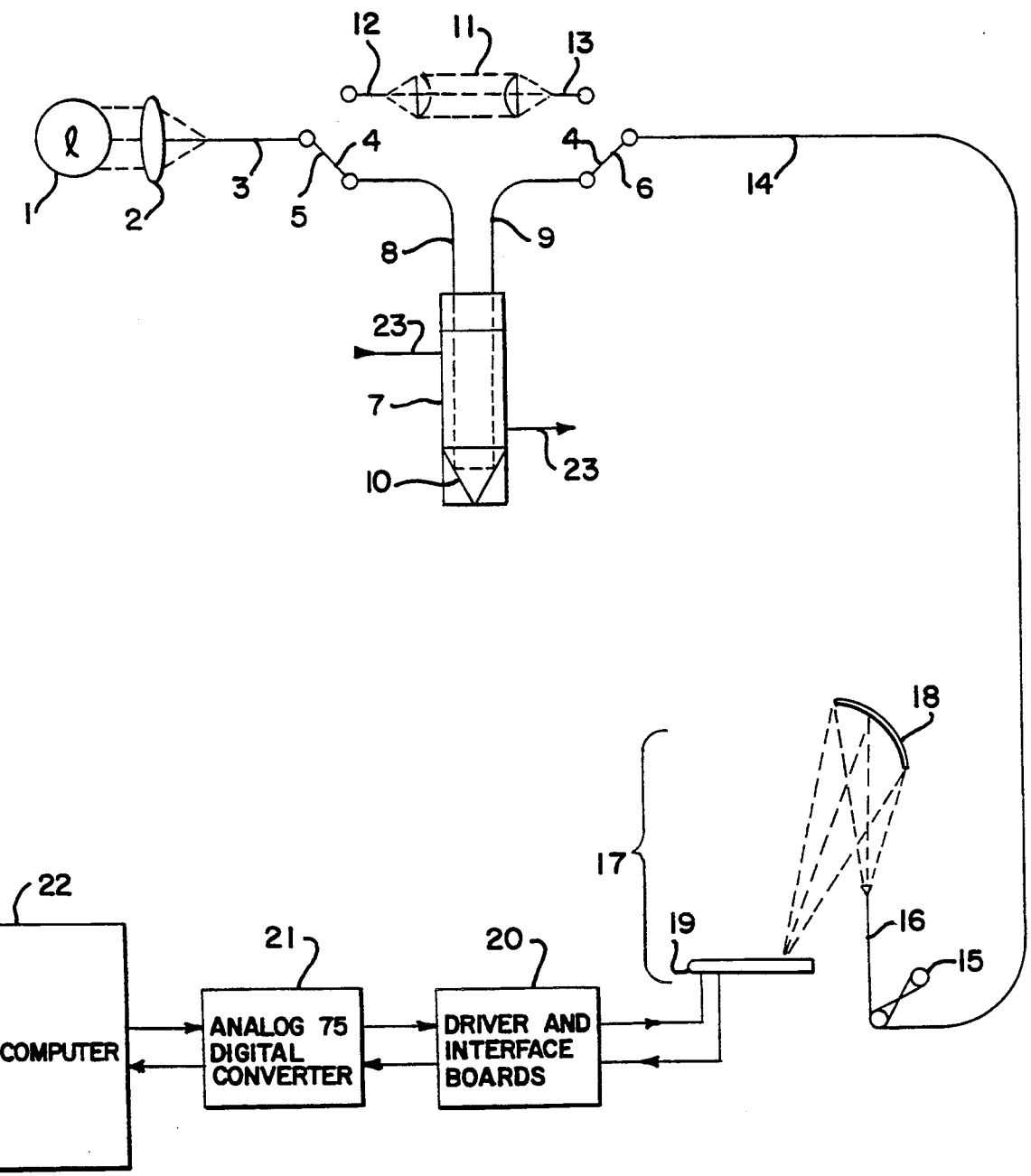
FIG. 1 is a diagram of a spectrophotometric device suitable for use with the method of the present invention.

The present invention refers to a method for transferring spectral information, including chemometric models, among spectrometers. For the purpose of the present invention, spectral information refers to light having wavelengths of 100 nanometers to about 2,500 nanometers including the ultraviolet (100 nanometers to about 400 nanometers), visible (400 nanometers to about 800 nanometers), and near-infrared (800 nanometers to about 2,500 nanometers) regions. Spectral images, for purpose of the present invention, are the particular spectra or segments of spectra, often described as the relationship of optical wavelength (x-axis) and absorbance, transmittance, light intensity, voltage, or the like (y-axis), corresponding to a particular spectrophotometric analysis.

The optical features of the near-infrared range, a range particularly suited for the analysis of the physical, chemical, and fuel properties of hydrocarbons, are generally combinations and overtones of vibrational modes found in the infrared (2,500 nanometers to about 25,000 nanometers). Generally, bonds of high asymmetry, such as carbonhydrogen and oxygen-hydrogen, create detectable and distinguishable features in the near-infrared region. However, much of the information in the near-infrared range is redundant. For example, the three carbonhydrogen overtones in the near-infrared range contain similar information as do the three carbon-hydrogen combination bands, and both sets of redundancies tend to result from similar chemistry. Calibration complexity and the potential for error can be minimized by avoiding consideration of redundant information.

Chemometric models are particularly useful for determining the composition of complex mixtures from their spectral information. Other mixture physical, chemical, and fuel properties can also be correlated to their spectral information where the property is related to the composition. Quantitative determinations are also well suited to spectrophotometric analysis, and in particular, spectrophotometric analysis utilizing near-infrared spectra. According to the Beer-Lambert law, absorbance (A) is proportional to the weight fraction of the absorbing species (W) as described in the following equations:

$$A = Log(I_o/I) = \epsilon L p W$$

where $I_o$ is the light intensity incident on the sample, I is the light intensity transmitted through the sample, $\epsilon$ is the absorption coefficient, L is the path length through the sample, and p is the bulk density of the sample. The transmittance is defined as the ratio of $I/I_o$. The absorbance can also change, indirectly, with the temperature of the sample due to thermal expansion, dissociation of the hydrogen bonds, and changes in the populations of energy levels associated with the absorption of the light intensity.

The spectral correlations used with the present invention are generally built utilizing the entire wavelength spectrum of the sample. Although a spectrum can consist of several hundred intensities measured at different wavelengths, many of these data points are highly interdependent, or collinear. Multivariate regression can be used to simplify the spectrum into latent vectors, which vary independently for a set of samples. The weights of the latent vectors in the spectrum change as the properties of the sample change. The number of latent vectors necessary to accurately model a system generally depends on the system being analyzed. Generally, the properties can be modeled using less than 20 latent vectors, frequently less than 10 latent vectors, and often less than 6 latent vectors. The number of latent vectors minimally necessary to predict stream compositions can be estimated using splitting techniques. PRESS statistics, plots of variance fit using successive numbers of latent vectors, or by other forms of statistical analysis.

The spectrometer suitable for use with the method of the present invention can span a broad wavelength range of from about 100 nanometers to about 2,500 nanometers or portions thereof where the particular feedstock determines which portions of the range of wavelengths are most desirable to use. Generally, most spectrometers suitable for use with the method of the present invention can be designed to span a range of from about 100 nanometers to about 1,100 nanometers, as narrow as from about 800 nanometers to about 1,100 nanometers, or even as narrow as from about 850 nanometers to about 1,000 nanometers.

Spectrometers spanning the range of from about 850 nanometers to about 1,000 nanometers include the third overtone of the carbonhydrogen stretching mode (850 nanometers to about 960 nanometers) and the second overtone of the oxygen-hydrogen stretching mode (960 nanometers to about 990 nanometers). The third combination band of the carbon-hydrogen stretching and bending modes is found at 1,000 nanometers to about 1,120 nanometers. However, this band can contain similar information to that found in the overtone bands and the spectra of this band can be noisy since the photoresponse of silicon detectors, found in photodiode arrays attendant to many spectrometers, can be substantially reduced above 1,000 nanometers. Spectrometers measuring the properties of pure and oxygenated hydrocarbons can generally analyze the properties of such a sample across a wavelength range of about 850 nanometers to about 1,000 nanometers.

FIG. 1 is a diagram of a spectrometer suitable for use with the method of the present invention. The light source 1 can be any suitable polychromatic light source such as tungsten, mercury vapor, tungsten filament lamps filled with an inert gas such as, but not limited to krypton, or with the filament under vacuum, and tungsten-halogen, with the preferred polychromatic light source being a tungsten-halogen lamp powered by a constant voltage or constant current supply. The output of light source 1 is launched through single lens 2 into fiber optic 3. The routing of light through the optics is controlled by two light switches 4 consisting of upstream light switch 5 and downstream light switch 6.

The polychromatic light from light source 1 can be directed in either of two directions: the sample channel direction or the reference channel direction. Polychromatic light generally travels through the sample channel direction when the light switches 4 are aligned to direct the polychromatic light to the sample cell 7 through fiber optic 8 and return the polychromatic light to downstream light switch 6 through fiber optic 9. Polychromatic light passes through the sample cell 7 where it is passed through sample stream 23 to be analyzed, strikes a prism or retroreflector 10, passes through sample stream 23 again, and is returned to fiber optic 9.

The polychromatic light from light source 1 can also travel though the reference channel direction when the light switches 4 are aligned to direct the polychromatic light to the attenuator 11 through fiber optic 12 and return the polychromatic light to downstream light switch 6 through fiber optic 13. The attenuator balances the polychromatic light transmission between the reference and sample channels and can consist of two lenses, preferably plano-convex lenses, in series or can be made without optics by separating the two fiber optics with a coupling device.

The polychromatic light passing through downstream light switch 6 is routed through fiber optic 14 to a mode scrambler 15. The mode scrambler 15 uniformly images light from the fiber optic into the spectrograph 17. A suitable mode scrambler 15 can compose fiber optic wrapped around two spools in a FIG. 8 pattern.

The polychromatic light from the mode scrambler 15 is passed through fiber optic 16 to the spectrograph 17 comprising a fixed diffraction grating 18 and a photodiode array detector 19. The polychromatic light from fiber optic 16 is launched onto the fixed diffraction grating 18 which diffracts and reflects the light onto the photodiode array detector 19.

Photodiode array detectors generally measure light intensity at all points in the spectrum simultaneously. Suitable photodiode array detectors can comprise metallurgy such as indium/gallium/arsenide, germanium, silicon, and silicon sensitized with platinum, with silicon being the preferred usage. Photodiode array detectors generally have elements, known as pixels, which correlate to the precise locations where light was diffracted and reflected from the fixed diffraction grating. Photodiode array detectors suitable for use with the method of the present invention generally have at least 100 pixels spanning the corresponding wavelength range of particular interest, preferably at least 200 pixels, and more preferably at least 500 pixels for best results. Corresponding pixel widths suitable for use with the method of the present invention should be at least I pixel per nanometer, preferably at least 2 pixels per nanometer, and more preferably at least 4 pixels per nanometer for best results. The resolution of the spectrometer should be less than 8 nanometers, preferably less than 4 nanometers, and more preferably less than 2 nanometers for best results.

Driver and Interface boards 20 are provided to drive the photodiode array detector 19, sequence the pixel readings, and amplify the signals prior to the analog to digital converter (ADC) 21. The interface boards 20 can comprise an amplifier section for conditioning the analog signal to the ADC 21, a crystal clock section for precisely sequencing the reading of the pixels, and a digital section for synchronizing the reading of the photoarray detector and triggering the ADC 21. The scan rate for scanning the photodiode array director 19 can be adjusted through the driver and interface boards 20 and generally ranges from about 10 to about 10 million pixels per second, preferably from about 1,000 to about 100,000 pixels per second, and more preferably from about 10,000 to about 100,000 pixels per second for best results.

The ADC 21 converts the light intensities from the photodiode array detector 19 into digital signals and is designed to be compatible with computer 22 or other means to digitally process spectral information. The computer 22 is provided to acquire, store, display, and analyze the spectra.

Spectrometers similar to that described in FIG. 1 and suitable for use with the method of the present invention generally function by launching polychromatic light alternatively through the sample and reference channels, through the fiber optic cable 14 to the mode scrambler 15, and onto the fixed diffraction grating 18. The polychromatic light from each channel is diffracted into its composite wavelengths and coordinated and recorded on a photodiode array detector 19.

Spectrometers having a sample and reference channel are referred to as dual-channel spectrometers. The reference channel measurements are provided to permit correction of the device for physical or mechanical changes that occur downstream of the downstream light switch 6. Physical changes in the device itself, the testing conditions, or any of a number of other events can create inaccuracies in the spectrophotometric readings. The spectrophotometric readings are also subject to photometric drift over time. Photometric drift can originate in the light source, the fiber optic cables, and other optical components, as well as the electronics utilized for measuring light intensity. Since polychromatic light travels through the same path through both the sample and reference channels, but for the fiber optic cable and other devices between the fiber optic switches, physical and mechanical changes and photometric drift that occur upstream or downstream of the fiber optic switches 4 can be factored out.

Light intensity is measured on the spectrometer and can generally be converted proportionally to an electrical signal. Suitable means for this conversion can include any one of a number of solid state electronic devices, including, but not limited to photodiode arrays, charge-coupled devices (CCD arrays), and optical sensor arrays. The solid state electronic device serves to convert the light signal to an electrical signal which is proportional to the light intensity. Thus the light intensity is converted to a electrical current, voltage, or charge signal which can be used as a convenient measure of light intensity. In this manner, photometric spectra are generally displayed with wavelength or pixel orientation on the x-axis and light intensity as measured by electrical current, voltage, or charge on the y-axis.

Intensity spectra are generally used for transferring chemometric calibrations since these spectra provide the raw images on the spectrometer and the mathematics for transforming the images are less complex. Transmittance and absorbance spectra are non-linear combinations of the intensity spectra of the sample and the reference channels, and mechanisms to facilitate transfer of chemometric calibrations utilizing these terms should be adjusted accordingly.

The light intensity signal measured on the sample channel is quantified by the following expression:

$$S_s = S_d + a_c a_s g\, I_o(e^{-A})$$

where $S_d$ is the dark signal; ac is the attenuation, or reduction in the amplitude of the light signal in the optics common to the sample and reference channels; $a_s$ is the attenuation in the optics unique to the sample channel; and g is the photometric gain (i.e. light intensity to electrical signal conversion factor). The dark signal, $S_d$, can be determined by measuring light intensity with the fiber optic switches juxtaposed with one of the switches directed towards the sample channel and the other switch directed towards the reference channel. The dark signal is measured and defined as the zero point of the light intensity or y-axis.

The light intensity signal measured on the reference channel is quantified by the following expression;

$$S_r = S_d + a_c a_r g\, I_o$$

where $a_r$ is the attenuation in the optics unique to the reference channel. The apparent absorbance measured on a dual-channel spectrometer is defined by the following expression:

$$A_a = log[(S_r - S_d)/(S_s - S_d)] = A_b + \epsilon L p W$$

where the background spectrum is defined as $A_b = log(a_r/a_s)$ and reflects the difference in light absorbance between the reference and sample paths with no sample present. The apparent absorbance, $A_a$, the background spectrum, $A_b$, the absorption coefficient, $\epsilon$, and to some extent, the path length L, are wavelength dependent. To first order, the apparent absorbance, $A_a$, in a dual-channel instrument is not a function of light intensity incident on the sample, $I_o$, common mode attenuation, $a_c$, and the photometric gain, g.

The expression for apparent absorbance, $A_a$, reveals three sources of variability among spectrometers: the background spectrum, the sample path length, and the wavelength scale. In order to accurately transfer chemometric models between spectrometers, these variables must be calibrated. To obtain accurate predictions on the target spectrometer, drift in these variables should also be minimized.

Transferring Chemometric Calibrations Among Spectrometers

The method of the present invention for transferring chemometric calibrations from a source spectrometer to a target spectrometer generally begins with measurement of the background spectrum of the source and target spectrometers for calibration adjustment of the target spectrometer in a subsequent step. This can be achieved by measuring the spectrum for each spectrometer utilizing an empty sample cell or filling the sample cell with a non-absorbing material. Non-absorbing materials suitable for use in determining the background spectrum can be, but are not limited to, carbon tetrachloride, carbon disulfide, fluorinert, and dry air. Carbon tetrachloride is particularly useful for chemometric calibrations for instrumentation providing hydrocarbon determinations in the NIR range since the refractive index of carbon tetrachloride is similar to that of many hydrocarbons. The background spectrum at the various pixel locations on the photodiode array detector (correlated to wavelength) is recorded for both the source and target spectrometers.

The ratio of sample path lengths for the source and target spectrometers can then be determined for calibration adjustment of the target spectrometer in a subsequent step, extracting principles from the above expressions. The ratio of path lengths of the source and target spectrometers is given by the ratio of the apparent absorbances of a standard pure compound less the background absorbances. A suitable standard pure compound can be, but is not limited to, components such as benzene, cyclohexane, isooctane, n-hexane, chloroform, and the like. Components such as benzene are preferred since they generally have large and narrow absorbance spectra. The spectrum of light absorbance against pixel location (or wavelength) is generated for the standard pure compound, on each spectrometer. The background spectrum light intensity is subtracted from the light absorbance of the spectrum generated for the standard pure compound, and the ratio of the light absorbance for every wavelength measured on each particular pair of spectrometers generally approaches a constant.

The wavelengths calibration for the source and target spectrometers can then be performed through the use of substantially monochromatic atomic lines. The wavelength calibration is most effectively performed when the wavelengths of the atomic lines meet the following criteria:

1) The wavelengths associated with the atomic lines are known with sufficient accuracy. The wavelengths of the atomic lines should generally be known with an accuracy within about 0.03 nanometers at 1 standard deviation, preferably within about 0.01 nanometers at 1 standard deviation, and more preferably within about 0.001 nanometers at 1 standard deviation for best results;

2) The intrinsic atomic line width is narrower than the resolution of the spectrometer at the wavelength of calibration. The resolution of the spectrometer generally exceeds the thickness of the atomic lines so that the mean and vadance of the atomic line as received can be determined with minimal ambiguity;

3) Where the atomic line source provides multiple atomic lines, the atomic lines should generally be spaced sufficiently distant in wavelength so as not to overlap, given the wavelength-resolving capabilities of the spectrometer to be calibrated; and 4) The atomic lines should be sufficiently intense to detect, utilizing the spectrometer to be calibrated.

The source of atomic lines should generally be selected so as to have a significant presence in the wavelengths to be utilized. Suitable means for generating light at well-defined wavelengths are through the use of arc lamps, plasma sources, lasers, diode lasers, hollow cathode lamps, and electrodeless discharge lamps.

Suitable atomic line sources which can be provided by monochromatic light in the wavelength region covering spectral information are the noble gases, halogens, hydrogen, alkali metals, alkaline earth metals, and rare earth metals, among other metals. The noble gases comprising neon, argon, krypton, and xenon are particularly useful in all or part of the near-infrared region. Krypton is also suitable for use in the visible range. Argon is particularly preferred in the wavelength range of from about 700 nanometers to about 1,050 nanometers. The halogens comprising fluorine, chlorine, bromine, and iodine are generally most useful in the wavelengths ranging from about 200 nanometers to about 1,000 nanometers. Bromine can also be useful up to about 2,500 nanometers. The alkali metals comprising sodium, rubidium, and cesium are particularly useful throughout the visible and ultraviolet ranges. Sodium and cesium are also suitable for use in wavelength ranges up to about 1,100 nanometers about 1,700 nanometers respectively. The alkaline earth metals comprising strontium and barium are useful in the visible range with strontium being useful up to about 1,050 nanometers. The rare earth metals comprising lanthanum, europium, erbium, dyspropium, and ytterbium are useful through parts of the visible and ultraviolet ranges. Other metals such as manganese, yttrium, zirconium, indium, tungsten, mercury, thallium, and lead are similarly suitable for use in parts of the visible and ultraviolet ranges.

The preferred atomic line sources for use in the near-infrared region are the noble gases, with argon being most preferred.

An argon monochromatic atomic line light source has known wavelengths and corresponding light intensities. The light intensity for argon applicable to the particular wavelengths, for purposes of the present invention, is generally expressed as a percentage of the total argon light intensity in the wavelength range of interest. The percentage of total light intensity term is generally utilized to identify the peaks corresponding to the particular atomic lines. Since light intensity is expressed as a fraction of total intensity and is generally provided for peak identification, the magnitude of the light intensity is not essential for purposes of the present invention. In fact, the calibration of the target spectrometer to the source spectrometer can be performed using two different argon lamps of differing intensities. A primary objective of the wavelength calibration activity is to correlate the pixel locations of the source spectrometer to the target spectrometer for each known wavelength provided by the atomic line source.

A material that absorbs or transmits light at known wavelengths can be utilized instead of a light source atomic line source. When utilizing a light-absorbing material, the baseline of the spectrum corresponds to 100% light transmission and the peaks are inverted where the particular absorption occurs. The calibration technique remains similar to that described for light source methods but for the reverse orientation of the light intensity/pixel orientation or wavelength function.

The atomic line source is launched through each of the source and target spectrometers, displaying a spectrum of light intensities at various wavelengths or pixel locations on each spectrometer. This can be performed by replacing the polychromatic light sources in each of the spectrometers with suitable monochromatic light sources. The source and target spectrometers generally show spectrums that vary in their placement along the x-axis (pixel alignment) and in their resolution.

The precise pixel alignment or orientation for the known wavelength corresponding to the atomic line for each spectrometer can then be determined. One method for determining the precise pixel location corresponding to the known wavelength is through a weighted mean calculation. This calculation is performed by numbering the pixels displaced along the photodiode array detector of the spectrometer. The leading edge of the $n^{th}$ pixel is assigned a distance of n-1 and the trailing edge, a distance of n. Fractional distances correspond to a certain position within a pixel. In this manner, displacement along an array of discrete elements can be represented as a continuous variable. The weighted mean average calculation can be expressed as follows:

$$\mu = \left[ \sum_1^k (n - 0.5)(S_n - S_o) \right] / \Sigma(S_n - S_o)$$

where there are k pixels in the series comprising the peak, the light intensity signal measured at pixel n, $S_n$, has been corrected for the dark signal, the displacement is defined by the convention noted above, and the baseline signal, $S_o$, which generally results from stray light, has been subtracted so that the mean can be determined accurately. This calculation is performed for all discernable lines for both the source and target spectrometers. In this manner, the wavelength along the photodiode array detector can be calibrated to an accuracy of generally less than 0.03 nanometers at 1 standard deviation, preferably less than 0.01 nanometers at 1 standard deviation, and more preferably less than 0.005 nanometers at 1 standard deviation, even though each pixel itself can cover a spectral range of up to 1 nanometer.

The atomic line resolution of the source and target spectrometers is then determined at the wavelength of the atomic line. The atomic line resolution, for purposes of the present invention, is measured as the variance of the image of the atomic line from the mean average pixel alignment at 1 standard deviation of pixel deviation from the precise mean average pixel alignment corresponding to each particular known wavelength generated from the atomic lines of the monochromatic light source. The atomic line resolution can be determined using the following expression:

$$\sigma^2 = \left[ \sum_1^k (n - 0.5)^2 (S_n - S_o) \right] / \Sigma(S_n - S_o) - \mu^2$$

where there are k pixels in the series of pixels comprising the peak. After the mean average pixel location and atomic line resolution are characterized for the wavelengths corresponding to each atomic line, values for other wavelengths can be calculated by methods such as linear interpolation or by extrapolation.

Once the mean average pixel location and atomic line resolution has been determined for the source and target spectrometers at the particular wavelengths corresponding to the monochromatic light source, a correlation can be developed for transferring the light intensity spectra from the source spectrometer to the target spectrometer. An objective of this correlation is to cause spectral images from a sample measured on the source spectrometer to appear substantially similar to the spectral images of the sample measured on the target spectrometer. A mathematical correlation is developed to relate the mean average pixel location of the source spectrometer (x-axis) to the mean average pixel location and the difference in atomic line resolution between the target and source spectrometers (y-axis), as a function of the mean average pixel location of the source spectrometer. For correlation of the mean average pixel location, this correlation can be, and is generally best represented by, a cubic polynomial expression such as the following:

$$P_t = C_o + C_1 P_S + C_2 P_S^2 + C_3 P_S^3$$

where $P_t$ is the pixel location on the target spectrometer and $P_s$ is the pixel location on the source spectrometer. The coefficient terms $C_o$, $C_1$, $C_2$, and $C_3$ can be determined through means such as linear regression utilizing the source and target spectrometer data points generated above. For many fixed-grating spectrometers, the coefficient terms $C_o$, $C_1$, $C_2$, and $C_3$ can also be approximated by the following expressions:

$$C_o = 2\ sin(\alpha/\omega)$$

$$C_1 = -cos(\alpha/\omega F_o)$$

$$C_2 = -C_o/4F_o^2$$

$$C_3 = -C_1/2F_o^2$$

where $\alpha$ is the angle of the diffraction grating relative to the plane that is perpendicular to the axis of the fiber optic that conveys the light onto the diffraction grating and parallel to the photodiode array detector, $\omega$ is the groove frequency of the diffraction grating, and $F_o$ is the focal distance between the fixed diffraction grating and the photodiode array detector.

The resolution adjustment is performed to blur the light intensity spectral images transformed from the source spectrometer in a manner such that it appears substantially similar to the images that would be measured on the target spectrometer. The atomic line resolution difference between the source and target spectrometers can be correlated utilizing the following expression:

$$\sigma_t^2 - (dP_t/dP_s)^2 \sigma_s^2 = D_0 + D_1 X_s + D_2 X_s^2 + D_3 X_s^3$$

where $\sigma_t$ is the resolution on the target spectrometer and $\sigma_s$ is the resolution on the source spectrometer and the coefficient terms $D_o$, $D_1$, $D_2$, and $D_3$ can similarly be determined through means such as linear regression utilizing the source and target spectrometer data points generated above. The derivative term in the expression accounts for the differences in the dispersion or the spectral ranges of the spectrometers and is evaluated at the wavelength of the atomic line.

Where the spectrometers have the same resolution, the weighted mean calculation is the general rule for transforming and mapping the light intensity spectra from the source spectrometer onto the target spectrometer. The range of where the light intensity of the $n^{th}$ pixel of the source spectrometer falls on the target spectrometer is determined by setting $P_s$ equal to n-1 and n. The light intensity is assumed to be uniformly distributed over the target range. More elaborate assumptions and methods can be utilized to determine the light intensity for mapping purposes, but are not essential to the accurate transfer of chemometric models among spectrometers.

Where the spectrometers have different resolutions, the light intensity is generally spread over a broader range on the target spectrometer. If the source spectrometer has a better resolution than the target spectrometer at all wavelengths, when $P_s$ is equal to (n−0.5), the expression for atomic line resolution provides the difference in resolution applicable for the $n^{th}$ pixel of the source spectrometer for use in mapping on the target spectrometer.

A convoluting function, whose pixel width depends on the resolution difference between the source and target spectrometers, is used to correct for resolution differences by first applying the weighted mean calculation to each pixel of the source spectrometer to determine where the light intensity will be transferred to on the target spectrometer. The light intensity is assumed to be uniformly distributed over the range, and this fixes the light intensity that falls on each pixel of the target spectrometer. The adjustment for resolution differences is made by centering the convoluting function over each pixel of the target spectrometer and redistributing the light intensity over adjacent pixels accordingly. The procedure is generally applied to each pixel of the source spectrometer. The results are superimposed to obtain the transformed light intensity spectra for the target spectrometer.

Where the target spectrometer has a better resolution than the source spectrometer, the intensity spectra of the target spectrometer can be blurred through convolution with a smoothing function so that the resolution of the source spectrometer is generally greater than that of the target spectrometer and the above procedures apply. Spectral deconvolution is not preferred because this method can be less accurate and is difficult to implement numerically. The width of the convoluting function is selected so that the resolution of the source spectrometer becomes greater than the resolution of the target spectrometer for all wavelengths of interest. Some spectral information can be lost through smoothing, but this is not restrictive if the spectrometer has suitable resolution.

The light intensity spectrum from the source spectrometer is remapped onto the target spectrometer utilizing software versions of the previously developed expressions, for each sample and reference spectra developed during the original calibration of the source spectrometer. Data points from each recorded sample spectra pixel point are extracted, converted to the corresponding target spectrometer pixel location, adjusted for resolution differences, and mapped on the target spectrometer. The pixel locations may not be, and are generally not, precisely centered within a pixel site and can overlap pixel ranges comprising several pixels. This is accommodated by weighting and interpolation to locate the precise target spectrometer pixel location. The light intensity dimension (y-axis) from the source machine is carried over to the precisely correlated pixel on the target machine in kind. The reference light intensity spectra for the source spectrometer is similarly remapped onto the target spectrometer using the same technique described above. In this manner, spectral images from a sample measured on the source spectrometer would appear substantially similar to the spectral images of the sample measured on the target spectrometer.

Accurate remapping of the source spectrometer sample light intensity spectra onto the target spectrometer can be performed for any number of sample spectra but are generally performed with from about 2 to about 300 sample spectra, preferably with from about 4 to about 100 sample spectra, and more preferably with from about 6 to about 30 sample spectra for best results. Reduced numbers of sample spectra can result in increased error in the chemometric calibration while high numbers of sample spectra can be costly and provide limited additional benefit.

The corrected reference light intensity spectrum for the source spectrometer is developed by dividing the spectrum developed earlier for a non-absorbing material such as carbon tetrachloride by the reference spectra for the source spectrometer on a pixel by pixel basis, which is measured shortly before or thereafter. The corrected reference light intensity curve corresponding to each sample is generated by multiplying the reference light intensity spectra for each pixel, measured shortly before or after the sample, by the above determined source spectrometer non-absorbing sample to reference spectra ratio. In this manner, a corrected reference intensity curve for the source spectrometer is generated for transformation onto the target spectrometer.

The absorbance spectrum is developed for the target spectrometer from the Beer-Lambert law as the log of the target spectrometer light intensity spectra for each of the original samples stored in the source spectrometer, divided by the corrected reference light intensity spectrum, corresponding to each sample, as follows:

$$Absorbance = log(I_o/I)$$

The absorbance spectrum is developed on a pixel by pixel basis. In this manner, a spectrum of absorbance against pixels or wavelength is provided that correlates precisely to the absorbance spectrum which could be measured on the target spectrometer.

It is understood that the absorbance spectra for the target spectrometer can be developed utilizing one, two, or several applications of the above described procedure. It is further understood that a plurality of transforming steps may be used and the chemometric model built and applied between any of these transforming steps. However, a single transformation is preferred for best accuracy and maximum computational speed.

An absorbance spectrum for the target spectrometer is then derived from the sample and reference light intensity spectra previously developed. The absorbance spectrum is derived by correcting the target light intensity spectrum for the difference in background spectra and sample path length between the target and source spectrometers previously determined, developing the corrected reference light intensity spectra for use on the target spectrometer which have been corrected for the background absorbance of the source spectrometer, and performing conversion of the light intensity spectra into absorbance.

The previously remapped target spectrometer absorbance spectra for each of the originally recorded samples is corrected for the difference in sample path length between the source and the target spectrometers. This is achieved by multiplying the previously calculated correction ratio for path length, determined as the ratio of the apparent absorbances of a standard pure compound less the background absorbance, to the sample absorbance spectrum developed for the target spectrometer. This ratio is generally a constant and applies linearly to all of the absorbance terms at each pixel for each sample.

The target spectrometer absorbance spectra (corrected for the path length difference in spectrometers) for each of the originally recorded samples is then augmented by the addition of the previously generated target spectrometer background spectrum. This is achieved by adding the previously determined background spectra for the target spectrometer, determined as the spectra from an empty sample cell or a sample cell containing a non-absorbing material, to the sample absorbance spectrum developed for the target spectrometer. This background correction, performed for each of the originally recorded sample data points, at each pixel location, completes the final adjusted absorbance spectrum for the target spectrometer.

The absorbance spectrum is then generally filtered to remove high frequency electronic noise and baseline drift. The absorbance spectrum, in its present form, can be subject to high frequency electronic noise, or the scattering of points above and below the absorbance spectrum that can be caused by anomalies in the electronics or optics. The absorbance spectrum, in its present form, can also experience baseline drift. Baseline drift occurs where the valley between peaks in an absorbance spectrum begins to drift upwards or downwards. Baseline drift generally is created from low frequency noise and can be caused by drift in the electronics, scattering by the sample, and thermal expansion in the optics. High frequency electronic noise and baseline drift can be eliminated by a filtering step.

Filtering high frequency electronic noise can be performed by smoothing or weight-averaging adjacent data points. Common algorithms for smoothing spectra can include Fourier filters, best-fit polynomials, Gaussian or binomial filters, and binning or adding groups of adjacent data points. Binomial filters are used most commonly since all of the methods provide similar accuracy while the binomial filters are easier to implement. Binning methods can be attractive since fewer data points can be used to represent the spectrum, thereby increasing computational speed. The extent of high frequency filtering is generally controlled by varying the number of points used in the smoothing algorithm.

Filtering low frequency noise is most commonly performed by differentiation. The extent of low frequency filtering is generally controlled by taking successive derivatives.

The new chemometric model is constructed from the filtered absorbance spectra to determine the physical properties of the samples to be monitored. Suitable methods for correlating the filtered absorbance spectra to the properties of a material, and selecting latent vectors or wavelengths for the correlation, can include, but are not limited to, partial least square (PLS) methods, principle components regression (PCR), and multi-linear regression (MLR). In principle components regression, each successive latent vector is correlated to the filtered absorbance spectrum in order of contribution to the total absorbance until substantially all of the absorbance can be described using linear combinations of the latent vectors. In partial least square methods, each successive latent vector is correlated to the filtered absorbance spectrum in order of contribution to the total absorbance, and the dependent variable, or property of the sample which is intended to be described using the absorbance spectra, until substantially all of the absorbance and all of the variations in the sample property can be described using linear combinations of the latent vectors. Suitable software packages for performing these functions are the PLS software written by the Center for Process Analytical Chemistry at the University of Washington (CPAC) and SpectraCalc, written by Galactic. The chemometric model is then generally tested for accuracy.

The method for transferring spectral information among spectrometers of the present invention provides outstanding accuracy. The method generally provides a transferred chemometric model on the target spectrometer (the spectrometer receiving the chemometric model) having nearly the same accuracy as the chemometric model on the source spectrometer (the spectrometer transferring the chemometric model). The increase in the standard error of prediction for the target spectrometer as compared to the source spectrometer is generally less than 100° percent relative to the standard error of prediction for the source spectrometer, generally less than 30° percent relative to the standard error of prediction for the source spectrometer, and can range as low as 10° percent relative to the standard error of prediction for the source spectrometer. For example, where the chemometric model on the source spectrometer has a standard error of prediction of 0.10° percent, the transferred chemometric model on the target machine would be transferred with an error of prediction of less than 0.20° percent, generally less than 0.13° percent, and often less than 0.11° percent. At the ranges of accuracy attendant to spectrometers suitable for use in conjunction with the method of the present invention, the accuracy levels of the target spectrometer and the source spectrometer are essentially equivalent.

The method for transferring spectral information among spectrometers of the present invention does not require the use of training or representative samples. An array of calibration samples is generally employed during the original calibration of the source spectrometer, but are not utilized or necessary after the initial calibration of the source spectrometer. Subsequent transfers of spectral information from the source spectrometer to one or more target spectrometers is performed directly from the source spectrometer or from data storage means, to the target spectrometer, through the method described. Eliminating the need for training or representative samples eliminates the need to handle, store, and administer sample storage. Training sample methods are also difficult and awkward to administer in an industrial environment, especially where the spectrometer is in a location that provides little maneuvering room or where the spectrometer is positioned in a location requiring special agility, such as the climbing of ladders. Similarly, these locations can also lack the requisite cleanliness to insure that the standards are kept pure and not contaminated.

The method for transferring spectral information among spectrometers of the present invention is simple and convenient and can be performed by a semi-skilled technician using a computer and a procedural guideline. The method of the present invention has been developed in a manner that requires the temporary removal of the polychromatic light source, replacement with a suitable monochromatic light source, and the execution of precise method steps that can be provided substantially through software. The method can be further simplified by incorporating the monochromatic light source directly into the spectrometer. Moreover, the source spectrometer spectral information can be recorded at any time prior to transfer of spectral information and can be provided through data storage devices separate and apart from the spectrometer such as data storage disks. This aspect of the present invention further minimizes the task complexity, the time required for transfer, and the potential for error. These factors are particularly critical when functioning in an industrial environment.

The method for transferring spectral information among spectrometers of the present invention can be performed without intervening decision-making steps by a skilled analyst. The method of the present invention requires minimal operator judgement, technical assessment, and decision-making skills beyond that of temporarily changing a light source and implementing software routines. This method can be executed in its entirety by instrumentation personnel such as those that routinely maintain, install, and calibrate conventional instrumentation in manufacturing facilities, chemical plants, petroleum refineries, and the like. This is particularly important in view of the fact that instrumentation personnel generally perform the repairs and activities that can initially cause a spectrometer to fall out of calibration. Similarly, instrumentation personnel can now be responsive to their end users directly, without involving the time and expense of outside expertise.

The present invention is described in further detail in connection with the following examples, it being understood that the same are for purposes of illustration and not limitation.

EXAMPLE 1

The accuracy of the method of the present invention for transferring chemometric models among spectrometers was tested as follows. Spectra of a sample set were measured independently on two separate spectrometers. The compositions of each sample in the set were known. The spectra of one of the spectrometers (source) was then transferred to the other (target) using the chemometric model transfer method of the present invention. A chemometric model was built from one of the two sets of spectra corresponding to the particular spectrometer and applied to the other set of spectra to predict the composition of the samples. Predicted and actual values determined from laboratory tests were compared to assess the errors. The bias in the predictions were utilized to distinguish the errors associated with transferring the models from the errors inherent in the model.

The sample set utilized in the testing procedure consisted of 29 samples containing varying amounts of n-heptane, iso-octane, toluene, para-xylene, and n-decane. The range of concentrations of the components in the samples and the average concentrations are described in Table 1.

TABLE 1

| SAMPLE SET COMPOSITION RANGES | | | |
|---|---|---|---|
| | Concentrations (Wt %) | | |
| Constituent | Minimum | Maximum | Average |
| n-heptane | 9.86 | 29.84 | 17.50 |
| i-octane | 9.92 | 29.90 | 20.92 |
| toluene | 29.96 | 49.95 | 38.75 |
| p-xylene | 3.94 | 15.28 | 9.41 |
| n-decane | 1.00 | 32.94 | 13.42 |
| n-alkanes | 14.85 | 47.10 | 30.91 |

In order to simulate the transfer of chemometric calibrations among spectrometers on different spectrometers, the two spectrometers were either reconfigured or alternated. The variables included the spectrograph (the diffraction grating and mechanical mountings), the photodiode array detector and detection electronics, and the mode scrambler. The hardware configurations and corresponding test numbers are described in Table 2.

TABLE 2

DIFFERENCES IN THE HARDWARE CONFIGURATION IN TESTS OF THE METHOD FOR TRANSFERRING CHEMOMETRIC MODELS

| Test # | Spectrograph | Mode Scrambler | Array Detector |
|---|---|---|---|
| 1 | − | + | − |
| 2 | − | − | − |
| 3 | + | − | − |
| 4 | − | − | + |

Notes:
1. The two spectrographs used were nominally identical, but produced very different spectra.
2. For the (−) cases, the mode scrambler was made by wrapping the fiber optic around two 0.5 in. diameter spools in a figure-eight pattern. For the (+) case, the mode scrambler was made from 700 ft. of 0.3 NA fiber, which launched into a short run of 0.2 NA fiber and then into the spectrograph.
3. For the (−) cases, a Reticon 1024S array was used. For the (+) case, a Reticon 1024SB array was used. Reticon evaluation boards were used to drive the arrays. The electronics driving the two arrays had different circuitry for photodetection.

The tests for chemometric model accuracy for the devices described in Table 2 were performed in a similar manner except that the intensity spectra were measured from 1,000 scans at a rate of 50 scans per second in all tests except for Test 1. In Test 1, 100 scans were used. The samples in the study were re-used, rather then discarded.

The wavelength axes were calibrated using atomic lines from an argon arc lamp. Table 3 provides qualities of the atomic lines obtained by calibrating each hardware configuration. Skewness was defined so that 0.5 was a symmetric peak, 0.0 was skewed entirely to the left, and 1.0 was skewed entirely to the right. Comparing Tests 1 and 2, where only the mode scrambler and focus of the spectrometer were changed between tests, it was apparent that subtle changes to the hardware could cause substantial shifts in the wavelength axis. Shifts of 0.03 pixels, or about 0.01 nanometers in the present example, can cause measurable errors in chemometric models. Table 3 indicates that a chemometric model developed for any test or device generally does not provide accurate results when applied directly to spectra measured in another test or device.

drogen-carbon stretching mode (840–965 nanometers) were ignored unless noted otherwise. The absorbance spectra were differentiated once to reduce the effects of baseline drift, and then smoothed over four pixels to filter pattern noise from the photodiode array detector electronics.

The chemometric models were built using the CPAC PLS program written by the Center for Process Analytical Chemistry at the University of Washington (CPAC). To enhance accuracy, spectra were scaled by mean centering. Four latent vectors were used to model the concentrations of the five constituents in the sample set. Four vectors are expected if no interactions between constituents occur.

The inherent errors in the chemometric models built from each test set are described in Table 4. These inherent errors are known as the Standard Error of Estimation (SEE). The SEE provides the standard deviation for a chemometric model built and used on a single spectrometer and is determined as the standard deviation between the values of the concentration predicted from the single spectrometer and laboratory measured values of the concentrations for the 29 samples. Therefore, the SEE is the minimum standard error that can be obtained when the test set is transferred to another spectrometer and measurements are made from a model built on that spectrometer. The SEE was largest for Test 4 since the sample set was last used for Test 4 and there may have been some sample contamination. Table 4 also lists the SEE for a chemometric model built using the combined data from tests 1 and 2 (1+2). In Test 1+2, the light intensity spectra from Test 1 was transformed to the wavelength axis of Test 2 to build the chemometric model. The fitted spectral variance is a measure of how much of the information in the spectra of the sample set is used to predict the properties of the sample set and is determined as the percentage of the variance in the spectra that can be fit or predicted by weighted use of the latent vectors.

TABLE 3

QUALITIES OF THE ARGON LINES OBTAINED BY CALIBRATING EACH HARDWARE CONFIGURATION (RELATIVE INTENSITIES WILL NOT SUM TO 100% BECAUSE THE LINES NEAR 842 NM AND WEAK LINES ARE IGNORED)

| Wavelength (nm) | Relative Intensity (X) | Mean (Pixel #) | Variance (Pixels Squared) | Skewness | Relative Intensity | Mean # (Pixel) | Variance (Pixels Squared) | Skewness |
|---|---|---|---|---|---|---|---|---|
| | TEST 1 | | | | TEST 2 | | | |
| 826.45 | — | — | — | — | 13.03 | 26.25 | 8.60 | 0.56 |
| 852.14 | 8.12 | 103.46 | 5.44 | 0.55 | 7.20 | 116.43 | 5.35 | 0.54 |
| 866.79 | 1.25 | 155.10 | 4.98 | 0.51 | 1.09 | 168.07 | 5.06 | 0.51 |
| 912.30 | 33.61 | 316.62 | 5.64 | 0.51 | 28.95 | 329.60 | 6.47 | 0.55 |
| 922.45 | 8.20 | 352.99 | 6.05 | 0.50 | 7.07 | 365.98 | 7.14 | 0.54 |
| 935.42 | 0.53 | 399.64 | 6.80 | 0.55 | 0.46 | 412.64 | 8.15 | 0.51 |
| 965.78 | 12.91 | 509.90 | 9.73 | 0.49 | 11.05 | 523.05 | 12.08 | 0.50 |
| 978.45 | 1.51 | 556.47 | 11.26 | 0.50 | 1.30 | 569.65 | 13.93 | 0.48 |
| 1047.00 | 2.59 | 815.05 | 23.76 | 0.50 | 2.09 | 828.82 | 26.22 | 0.49 |
| | TEST 3 | | | | TEST 4 | | | |
| 826.45 | 12.62 | 40.90 | 10.28 | 0.56 | 12.41 | 46.94 | 9.28 | 0.53 |
| 852.14 | 7.03 | 130.59 | 5.68 | 0.55 | 6.88 | 139.43 | 5.45 | 0.54 |
| 866.79 | 1.07 | 181.99 | 5.18 | 0.50 | 1.06 | 192.43 | 4.68 | 0.54 |
| 912.30 | 29.27 | 343.32 | 7.22 | 0.49 | 31.16 | 358.18 | 5.69 | 0.52 |
| 922.45 | 7.14 | 379.66 | 8.48 | 0.51 | 6.84 | 395.49 | 6.34 | 0.54 |
| 935.42 | 0.46 | 426.36 | 10.20 | 0.49 | 0.45 | 443.41 | 7.45 | 0.53 |
| 965.78 | 11.39 | 537.03 | 16.56 | 0.50 | 11.07 | 556.66 | 11.05 | 0.54 |
| 978.45 | 1.32 | 583.70 | 19.07 | 0.51 | 1.23 | 604.41 | 12.44 | 0.53 |
| 1047.00 | 2.22 | 843.74 | 33.31 | 0.51 | 1.24 | 870.06 | 21.18 | 0.53 |

The spectra were filtered prior to modeling and prediction. Regions outside the third overtone of the hy-

TABLE 4

INHERENT ERRORS (STANDARD ERRORS OF ESTIMATION) IN MODELS BUILT FROM EACH SAMPLE SET

| Test # | 1 | 2 | 3 | 4 | 1 + 2 |
|---|---|---|---|---|---|
| SEE (Wt %) | | | | | |
| n-heptane | 0.51 | 0.42 | 0.49 | 0.52 | 0.56 |
| i-octane | 0.15 | 0.17 | 0.31 | 0.35 | 0.18 |
| toluene | 0.11 | 0.15 | 0.28 | 0.56 | 0.14 |
| p-xylene | 0.11 | 0.11 | 0.18 | 0.16 | 0.12 |
| n-decane | 0.46 | 0.39 | 0.54 | 0.77 | 0.49 |
| n-alkanes | 0.16 | 0.17 | 0.28 | 0.47 | 0.19 |
| Fitted Spectral Variance (%) | 99.85 | 99.96 | 99.94 | 99.81 | 99.81 |

EXAMPLE 2

The chemometric models were transferred between the spectrometers described in Table 2 utilizing the method of the present invention. For each chemometric model transfer, the bias and the Standard Error of Prediction (SEP) were determined. The bias was determined as the average offset between the values of the concentration predicted from the target spectrometer and laboratory-measured values of the concentration for the 29 samples. The bias determination is an indicator of the error from transferring the model between instruments. The SEP was determined as the standard deviation between the values of the concentration predicted from the target spectrometer and laboratory measured values of independent samples. The SEP includes the errors inherent in building the model and transferring it between spectrometers. The results are provided in Table 5.

TABLE 5

RESULTS FROM TRANSFERRING CHEMOMETRIC MODELS AMONG INSTRUMENTS

| Source | 2 | 2 | 3 | 1 | 1 + 2 | 1 + 2 | 4 |
|---|---|---|---|---|---|---|---|
| Target | 3 | 3 | 2 | 2 | 3 | 3 | 2 |
| Modeling Set | 3 | 2 | 2 | 2 | 3 | 1 + 2 | 2 |
| Bias (Wt %) | | | | | | | |
| n-heptane | −0.15 | 0.07 | −0.01 | −0.54 | −0.41 | 0.39 | −0.84 |
| i-octane | 0.04 | −0.03 | −0.01 | 0.17 | 0.13 | −0.13 | 0.63 |
| toluene | 0.03 | −0.03 | −0.02 | 0.14 | 0.10 | −0.10 | −0.78 |
| p-xylene | 0.07 | −0.07 | −0.08 | −0.13 | −0.01 | 0.01 | −0.18 |
| n-decane | 0.05 | 0.02 | 0.11 | 0.35 | 0.22 | −0.20 | 1.14 |
| n-alkanes | −0.10 | 0.09 | 0.11 | −0.19 | 0.20 | 0.19 | 0.32 |
| SEP (Wt %) | | | | | | | |
| n-heptane | 0.45 | 0.48 | 0.47 | 0.75 | 0.72 | 0.64 | 1.01 |
| i-octane | 0.25 | 0.35 | 0.36 | 0.22 | 0.29 | 0.38 | 0.72 |
| toluene | 0.23 | 0.31 | 0.32 | 0.18 | 0.26 | 0.34 | 0.97 |
| p-xylene | 0.14 | 0.20 | 0.20 | 0.17 | 0.14 | 0.19 | 0.25 |
| n-decane | 0.44 | 0.57 | 0.56 | 0.60 | 0.16 | 0.64 | 1.37 |
| n-alkanes | 0.23 | 0.30 | 0.31 | 0.26 | 0.32 | 0.36 | 0.59 |

Chemometric models were transferred very accurately between instruments having different spectrographs as evidenced from transfers involving the spectrometers of Tests 2 and 3. Spectrometer 2 had a better resolution at all wavelengths than Spectrometer 3, yet models were transferred very accurately regardless of whether the target spectrometer had a higher or lower resolution.

Chemometric models transferred from Spectrometer 1 or from Spectrometer 1 in combination with Spectrometer 2 showed some bias. However, the standard errors of prediction described in Table 5 were similar to the inherent errors in the models described in Table 4. The bias decreased with successive spectra in Test 1, indicating that the bias as due to drift in the wavelength axis, rather than inaccuracies in the method for transferring chemometric models. The bias was smaller than the inherent error in the chemometric model, further indicating that the model was transferred accurately.

Chemometric models transferred from Test 4 had the largest biases, yet predictions from the transferred chemometric models were accurate to better than one part in twenty over the concentration ranges studied.

EXAMPLE 3

The effects of varying the spectral wavelength range on the accuracy of the method for transferring chemometric calibrations was measured utilizing Spectrometer 2 as the source spectrometer and Spectrometer 3 as the target spectrometer.

The spectral ranges examined were the overtone range of from about 850 nanometers to about 965 nanometers, the combination band range of from about 970 nanometers to about 1,075 nanometers, and the overall combined range of from about 850 nanometers to about 1,075 nanometers. The statistics of the models built from these spectra wavelength ranges are described in Table 6.

TABLE 6

STATISTICS OF MODELS BUILT FROM DIFFERENT SPECTRAL REGIONS UTILIZING SPECTROMETER 2

| | 850–965 nm | 850–1075 nm | 970–1075 nm |
|---|---|---|---|
| SEE (Wt %) | | | |
| n-heptane | 0.41 | 0.39 | 0.28 |
| i-octane | 0.16 | 0.16 | 0.20 |
| toluene | 0.15 | 0.15 | 0.33 |
| p-xylene | 0.11 | 0.11 | 0.32 |
| n-decane | 0.39 | 0.38 | 0.32 |
| n-alkanes | 0.17 | 0.17 | 0.16 |
| Fitted Spectral Variance (%) | 99.95 | 99.94 | 99.54 |

Information contained in the overtone (850 nanometers to 965 nanometers) and combination (970 nanometers to 1,075 nanometers) bands tends to be similar so that chemometric models built from one or both bands have similar standard errors of estimation. However, it is apparent that the standard errors of estimation are higher if the combination band is used alone to model the concentrations of toluene and xylene. This occurs since absorbances associated with aromatic compounds generally occur in the noisiest part of the combination band.

The chemometric models were transferred from Spectrometer 2 to Spectrometer 3 utilizing the method of the present invention for each of the three spectral wavelength ranges described above. The results of the accuracy of the chemometric model transfers are described in Table 7.

TABLE 7

RESULTS FROM TRANSFERRING MODELS BUILT FROM DIFFERENT SPECTRAL WAVELENGTH REGIONS

|  | 850–965 nm | 850–1075 nm | 970–1075 nm |
|---|---|---|---|
| Bias (Wt %) | | | |
| n-heptane | 0.07 | 0.19 | 1.17 |
| i-octane | −0.03 | −0.06 | −0.64 |
| toluene | −0.03 | −0.08 | −2.00 |
| p-xylene | −0.07 | 0.00 | 2.20 |
| n-decane | 0.02 | −0.08 | −0.77 |
| n-alkanes | 0.09 | 0.10 | 0.40 |
| SEP (Wt %) | | | |
| n-heptane | 0.49 | 0.50 | 1.39 |
| i-octane | 0.36 | 0.36 | 0.76 |
| toluene | 0.32 | 0.33 | 2.12 |
| p-xylene | 0.20 | 0.18 | 2.27 |
| n-decane | 0.58 | 0.57 | 1.11 |
| n-alkanes | 0.30 | 0.30 | 0.50 |

The overtone band was transferred accurately while biases were higher for the combination band. Only two detectable argon atomic lines occurred across the combination band where the resolution was the poorest. Six atomic lines occurred across the overtone band where the resolution was two times better. In this particular embodiment, chemometric models built from the overtone band were transferred more accurately. Chemometric models built from both bands transfer with generally similar accuracy as models built from the overtone band alone because the intense spectral variations in the overtone region can cause this region to be emphasized during modeling. The combination band can be omitted from the range of the spectrograph while maintaining similar chemometric model transfer accuracy. Where the combination band is omitted, the photodiode array detector can be reduced to about half the size, reducing hardware costs.

EXAMPLE 4

The effects of varying the number of argon atomic lines used for wavelength calibration on the accuracy of the method for transferring chemometric calibrations was measured utilizing Spectrometer 2 as the source spectrometer and Spectrometer 3 as the target spectrometer.

Nine atomic lines were detected across the full range of the spectrometer. Chemometric model transfer accuracy was determined for three separate cases including the four most intense lines in the overtone region, six lines in the overtone region, and nine lines spanning the range of the spectrometer. The accuracy results of the chemometric model transfers are described in Table 8.

TABLE 8

RELATIONSHIP BETWEEN THE NUMBER OF CALIBRATION LINES AND THE ACCURACY OF TRANSFERRING CHEMOMETRIC MODELS

|  | Nine Lines Between 820–1060 nm | Six Lines Between 850–980 nm | Lines at 852, 912, 922, and 966 nm |
|---|---|---|---|
| Bias (Wt %) | | | |
| n-heptane | 0.07 | 0.02 | 0.24 |
| i-octane | −0.03 | −0.03 | −0.05 |

TABLE 8-continued

RELATIONSHIP BETWEEN THE NUMBER OF CALIBRATION LINES AND THE ACCURACY OF TRANSFERRING CHEMOMETRIC MODELS

|  | Nine Lines Between 820–1060 nm | Six Lines Between 850–980 nm | Lines at 852, 912, 922, and 966 nm |
|---|---|---|---|
| toluene | −0.03 | −0.06 | 0.21 |
| p-xylene | −0.07 | −0.03 | −0.33 |
| n-decane | 0.02 | 0.06 | −0.11 |
| n-alkanes | 0.09 | 0.09 | 0.13 |
| SEP (Wt %) | | | |
| n-heptane | 0.49 | 0.49 | 0.54 |
| i-octane | 0.36 | 0.36 | 0.37 |
| toluene | 0.32 | 0.33 | 0.37 |
| p-xylene | 0.20 | 0.19 | 0.39 |
| n-decane | 0.58 | 0.58 | 0.57 |
| n-alkanes | 0.30 | 0.30 | 0.32 |

The nine line case provided outstanding chemometric model transfer accuracy. Where six lines in the overtone region were utilized, chemometric model transfer accuracy was similar to that of the nine line case. Where only the four most intense lines in the overtone region were used, the models were transferred with some bias. Thus, utilizing all of the detectable atomic lines in the overtone region can provide outstanding chemometric model transfer, similar to that of chemometric model transfers utilizing all detectable spectrometer lines including those beyond the overtone region.

EXAMPLE 5

The effects of varying the spatial resolution of the wavelength axis on the accuracy of the method for transferring chemometric calibrations was measured utilized Spectrometer 2 as the source spectrometer and Spectrometer 3 as the target spectrometer.

Spatial resolution was analyzed by adding the intensities of groups of adjacent pixels into the software. The accuracy of the method for transferring chemometric calibrations was determined with 400 pixels spanning the overtone region (about 3.5 pixels per nanometer), 200 pixels spanning the overtone region (about 1.7 pixels per nanometer), and 100 pixels spanning the overtone region (about 0.9 pixels per nanometer). The results of the accuracy of the chemometric model transfers are described in Table 9.

TABLE 9

RELATIONSHIP BETWEEN THE SPATIAL RESOLUTION OF THE WAVELENGTH AXIS AND THE ACCURACY OF TRANSFERRING CHEMOMETRIC MODELS

| No. of Pixels in the Overtone Region | 400 | 200 | 100 |
|---|---|---|---|
| Bias (Wt %) | | | |
| n-heptane | 0.07 | −0.06 | −0.87 |
| i-octane | −0.03 | 0.09 | 0.77 |
| toluene | −0.03 | 0.02 | 0.51 |
| p-xylene | −0.07 | −0.19 | −1.04 |
| n-decane | 0.02 | 0.09 | 0.58 |
| n-alkanes | 0.09 | 0.04 | −0.29 |
| SEP (Wt %) | | | |
| n-heptane | 0.49 | 0.55 | 1.56 |
| i-octane | 0.36 | 0.36 | 0.88 |
| toluene | 0.32 | 0.31 | 0.60 |
| p-xylene | 0.20 | 0.27 | 1.08 |
| n-decane | 0.58 | 0.64 | 1.30 |
| n-alkanes | 0.30 | 0.28 | 0.43 |

Where 400 pixels were dispersed across the overtone region (3.5 pixels per nanometer), chemometric model transfer accuracy was outstanding. Reducing the number of pixels to 200 pixels dispersed across the overtone region (1.7 pixels per nanometer) provided similar chemometric model transfer accuracy. Decreasing the number of pixels to 100 pixels dispersed across the overtone region (0.9 pixels per nanometer) decreased chemometric model transfer accuracy substantially. The loss of accuracy was not generally caused by the loss of resolution in the spectra but by less accuracy in the calibration of the wavelength axis. Using a photodiode array detector with fewer pixels is desirable for cost reduction purposes providing the number of pixels in the range to be monitored are adequate for accurate calibration of the wavelength axis.

That which is claimed is:

1. A method for transferring spectral information, comprising spectral images, from a source spectrometer to a target spectrometer for transferring chemometric models from said source spectrometer to said target spectrometer, comprising the steps of:
   (a) passing substantially monochromatic light into said source and target spectrometers and displaying a spectrum of light intensity at various wavelengths for each spectrometer;
   (b) developing a correlation between said spectra of light intensities at various wavelengths such that the location and shape of said target spectrometer correlated spectrum of light intensity at various wavelengths derived from said substantially monochromatic light is expressed as a function of said source spectrometer spectrum of light intensity at various wavelengths derived from said substantially monochromatic light;
   (c) processing a sample having known physical properties into said source spectrometer and displaying spectral images;
   (d) developing a transformation for said spectral images from said source spectrometer such that said correlated and transformed spectral images are transformed to appear substantially similar to said spectral images of said sample measured with said target spectrometer; and
   (e) generating a chemometric model to relate said correlated and transformed spectral images from said target spectrometer to said physical properties of said sample corresponding to said spectral images.

2. The method of claim 1 wherein said source and target spectrometers are dual-channel spectrometers.

3. The method of claim 1 wherein said monochromatic light is provided by an arc lamp comprising at least one member selected from the group consisting of argon, xenon, krypton, helium, radon, and neon.

4. The method of claim 1 wherein said spectral information transferred from said source spectrometer is transferred indirectly from an information storage device separate and apart from said spectrometer.

5. The method of claim 1 wherein said target spectrometer is an on-line analyzer.

6. The method of claim 1 wherein said transformation comprises a cubic polynomial.

7. A method for transferring spectral information, comprising spectral images, from a source dual-channel spectrometer to a target dual-channel spectrometer for transferring chemometric models from said source spectrometer to said target spectrometer, comprising the steps of:
   (a) measuring the background spectra corresponding to said source and target dual-channel spectrometers;
   (b) passing substantially monochromatic light comprising monochromatic atomic lines into said source and target dual-channel spectrometers and displaying a spectrum of light intensity at various wavelengths for each spectrometer;
   (c) developing a correlation between said spectra of light intensities at various wavelengths such that the wavelength scale of said target dual-channel spectrometer correlated spectrum of light intensity at various wavelengths derived from said substantially monochromatic light is expressed as a function of said source dual-channel spectrometer spectrum of light intensity at various wavelengths derived from said substantially monochromatic light;
   (d) processing a sample having known physical properties into said source dual-channel spectrometer and displaying spectral images;
   (e) developing a transformation for said spectral images from said source dual-channel spectrometer such that said correlated and transformed spectral images are transformed to appear substantially similar to said spectral images of said sample measured with said target dual-channel spectrometer;
   (f) adjusting said correlated and transformed spectral images for the differences in said background spectra between said source and target dual-channel spectrometers and creating adjusted correlated and transformed spectral images;
   (g) creating an absorbance spectra from said adjusted correlated and transformed spectral images; and
   (h) generating a chemometric model to relate said absorbance spectra from said target dual-channel spectrometer to said physical properties of said sample corresponding to said spectral images.

8. The method of claim 7 wherein said monochromatic light is provided by an arc lamp comprising at least one member selected from the group consisting of argon, xenon, krypton, helium, radon, and neon.

9. The method of claim 7 wherein said monochromatic light is provided utilizing a light-transmitting material, said light-transmitting material transmitting light having a wavelength between about 100 nanometers and about 2,500 nanometers.

10. The method of claim 7 wherein said spectral information transferred from said source dual-channel spectrometer is transferred indirectly from an information storage device separate and apart from said source dual-channel spectrometer.

11. The method of claim 7 wherein said target dual-channel spectrometer is an on-line analyzer.

12. The method of claim 7 wherein said transformation comprises utilizing not more than 9 atomic lines for said correlation between said wavelength scales.

13. The method of claim 7 wherein said target spectrometer comprising said generated chemometric model to relate said spectral images from said target spectrometer to said physical properties of said sample corresponding to said spectral images is utilized to determine at a least one physical property of at least one sample.

14. The method of claim 7 wherein said generating step comprises utilization of at least one method selected from the group consisting of partial least squares, principal components regression, and multi-linear regression.

15. The method of claim 7 wherein said monochromatic light has a wavelength ranging from about 100 nanometers to about 1100 nanometers.

16. The method of claim 7 wherein the source dual-channel spectrometer is the target dual-channel spectrometer.

17. A method for transferring spectral information comprising spectral images, from a source dual-channel spectrometer to a target dual-channel spectrometer, each having a sample cell path length, for transferring chemometric models from said source spectrometer to said target spectrometer, comprising the steps of:
(a) measuring the background spectra corresponding to said source and target dual-channel spectrometers;
(b) quantifying the path length ratio of said target and source dual-channel spectrometers;
(c) passing substantially monochromatic light comprising monochromatic atomic lines into said source and target dual-channel spectrometers and displaying a spectrum of light intensity at various wavelengths for each spectrometer;
(d) developing a correlation between said spectra of light intensities at various wavelengths such that the wavelength scale of said target dual-channel spectrometer correlated spectrum of light intensity at various wavelengths derived from said substantially monochromatic atomic lines can be expressed, utilizing a statistical method or correlation, as a function of said source dual-channel spectrometer spectrum of light intensity at various wavelengths derived from said substantially monochromatic light;
(e) processing a sample having known physical properties into said source spectrometer and displaying spectral images;
(f) developing a transformation for said spectral images from said source dual-channel spectrometer such that said correlated and transformed spectral images are transformed to appear substantially similar to said spectral images of said sample measured with said target dual-channel spectrometer;
(g) adjusting said correlated and transformed spectral images for the differences in said background spectra between, and said path length ratio of said source and target dual-channel spectrometers and creating adjusted correlated and transformed spectral images;
(h) creating an absorbance spectra from said adjusted correlated and transformed spectral images;
(i) filtering said absorbance spectra to minimize the effects of baseline drift and high frequency noise and creating a filtered absorbance spectra; and
(j) generating a chemometric model to relate said filtered absorbance spectra from said target dual-channel spectrometer to said physical properties of said sample corresponding to said spectra images.

18. The method of claim 17 wherein said monochromatic light is provided by an arc lamp comprising argon.

19. The method of claim 17 wherein said monochromatic light is provided utilizing a light-transmitting material, said light-transmitting material transmitting light having a wavelength between about 100 nanometers and about 1,100 nanometers.

20. The method of claim 17 wherein said monochromatic spectral images have a wavelength ranging from about 850 nanometers to about 1,000 nanometers.

21. The method of claim 17 wherein said spectral information transferred from said source spectrometer is transferred indirectly from an information storage device separate and apart from said spectrometer.

22. The method of claim 17 wherein said source and target dual-channel spectrometers each have a resolution of better than 2 nanometers.

23. The method of claim 17 wherein said measuring of said background spectra comprises measuring the transmittance of a substantially non-light absorbing material.

24. The method of claim 17 wherein said statistical method of correlation comprises a cubic polynomial.

25. The method of claim 17 wherein said generating step comprises utilization of at least one method selected from the group consisting of partial least squares, principal components regression, and multi-linear regression.

26. The method of claim 17 wherein the source dual-channel spectrometer is the target dual-channel spectrometer, and said spectrometer is being recalibrated.

27. The method of claim 17 wherein said target spectrometer comprising said generated chemometric model to relate said spectral images from said target spectrometer to said physical properties of said sample corresponding to said spectral images is utilized to determine at least one physical property of at least one sample.

28. A process for transferring spectral information, comprising spectral images, from a source spectrometer to a target spectrometer for transferring chemometric models from said source spectrometer to said target spectrometer and utilizing said target spectrometer to determine at least one physical property of at least one sample, comprising the steps of:
(a) passing substantially monochromatic light into said source and target spectrometers and displaying a spectrum of light intensity at various wavelengths for each spectrometer;
(b) developing a correlation between said spectra of light intensities at various wavelengths such that the location and shape of said target spectrometer correlated spectrum of light intensity at various wavelengths derived from said substantially monochromatic light can be expressed as a function of said source spectrometer spectrum of light intensity at various wavelengths derived from said substantially monochromatic light;
(c) processing a sample having known physical properties into said source spectrometer and displaying spectral images;
(d) developing a transformation for said spectral images from said source spectrometer such that said correlated and transformed spectral images are transformed to appear substantially similar to said spectral images of said sample measured with said target spectrometer;
(e) generating a chemometric model to relate said correlated and transformed spectral images form said target spectrometer to said physical properties of said sample corresponding to said spectral images; and
(f) utilizing said target spectrometer to determine at least one physical property of at least one sample.

* * * * *